US006503941B2

(12) United States Patent
Pyo et al.

(10) Patent No.: US 6,503,941 B2
(45) Date of Patent: Jan. 7, 2003

(54) FERULIC ESTER DERIVATIVE, 3,9-DIFERULYLCOUMESTROL AND COSMETIC PRODUCT CONTAINING SAME

(75) Inventors: Hyeong-Bae Pyo, Chungchongbuk-do (KR); Chung-Woo Lee, Chungchongbuk-do (KR); Sung-Min Park, Chungchongbuk-do (KR); Young-Ho Cho, Chungchongbuk-do (KR); Jeong-Jae Lee, Chungchongbuk-do (KR); Jin-Hwa Kim, Chungchongbuk-do (KR)

(73) Assignee: Hanbul Cosmetics Co., Ltd., Seoul (KR)

( * ) Notice: Subject to any disclaimer, the term of this patent is extended or adjusted under 35 U.S.C. 154(b) by 0 days.

(21) Appl. No.: 10/069,555
(22) PCT Filed: Jun. 21, 2001
(86) PCT No.: PCT/KR01/01059
  § 371 (c)(1),
  (2), (4) Date: Feb. 22, 2002
(87) PCT Pub. No.: WO01/97769
  PCT Pub. Date: Dec. 27, 2001

(65) Prior Publication Data
  US 2002/0160028 A1 Oct. 31, 2002

(30) Foreign Application Priority Data
  Jun. 23, 2000 (KR) .................. 2000-0034790

(51) Int. Cl.$^7$ .................. A61K 7/48; C07D 493/22
(52) U.S. Cl. .................. 514/453; 549/279
(58) Field of Search .................. 549/279; 514/453

(56) References Cited

U.S. PATENT DOCUMENTS 6,030,620 A * 2/2000 Pillai et al. .............. 424/195.1

FOREIGN PATENT DOCUMENTS

JP   09-040613   *  2/1997

OTHER PUBLICATIONS

M. Oshima et al., Matrix vol. 13, pp. 187–194 (1993) Active Oxygen–Induced Modification Alters Properties of Collagen as a Substratum for Fibroblasts.

S. Harumiya et al., J. Biocham., 120, 745–751(1996) Characterization of Ficolins as Novel Elastin–Binding Proteins and Molecular Cloning of Human Ficolin–1.
A. Hayasho et al., Fragnance J., 2, 32(1992).
L.H. Kligman et al., J.Invnest. Dermatol. 93, 210 (1989) Collagen Metabolism in Ultraviolet Irradiated Hairless Mouse Skin and Its Correlation to Histochemical Observations.
H. Tanaka et al., Arch. Dermatol. Res., 285, 352(1993) The effect of reactive oxygen species on the biosynthesis of collagen and glycosaminoglycans in cultured human dermal fibroblasts.
M.D. Carbonare et al., J. Photochem. Photobiol B. Biol., 14, 105(1992) Skin photosensitizing agents and the role of reactive oxygen species in photoaging.
T. Okada et al., Fragnance J., 11,23 (1993).
T.Shibamoto et al., American Chem Soc 154–165 (1994) Flavonoid with Strong Antioxidative Activity Isolated from Young Green Barley Leaves.
H.Hiasiwetz et al., Ann. 138, 61(1866) Mitteilungen aus dem chemischen Labcratorium in Innsbruck.
A.M. Klingman et al., J.Am. Acad. Dermatol., 15,836(1986) Tropical tretinoin for photoaged skin.
E.J. Van Scott et al., Cutis., 43, 222(1989) Alpha Hydroxy Acids: Procedures for Use in Clinical Practice.
M.G. Smart et al., Aust. J. Plant Physiol. 6, 485(1979).
T.Tsukiya et al., Jpn. Kokai 751862 (1975).
C.A. 83, 7602v(1975).
Darbarwar, M., et al., J. Sci. Ind. Res., 35, 297(1982).
Harborne et al., Phytochemical Dictionary, Taylor & Francis, London, pp 418(1993).
Bickoff, E.M., et al., J. Anim. Sci., 19, 4(1960) Some Variation in Estrogenic Activity in Fresh and Dried White Clover Clones and the Ladino Variety.
Bickoff, E.M., et al., J. Am. Chem. Soc., 80,4381 (1958).

* cited by examiner

*Primary Examiner*—Bernard Dentz
(74) *Attorney, Agent, or Firm*—Merchant & Gould P.C.

(57) ABSTRACT

The present invention relates to a skin cosmetic product containing 3,9-diferulylcoumestrol, especially to a skin cosmetic product containing a compound in which ferulylic acid is bonded to a coumestrol. The skin cosmetic product has several excellent effects for improving cosmetic disorders, such as anti-aging effect, whitening effect and hair-seeding effect.

4 Claims, 2 Drawing Sheets

Unapplied(Immediately after the experiment was started)

1,3-BG applied(after 2 weeks)

3,9-Diferulylcoumestrol applied (after 2 weeks)

1,3-BG applied(after 4 weeks)

3,9-Diferulylcoumestrol applied (after 4 weeks)

FERULIC ESTER DERIVATIVE, 3,9-DIFERULYLCOUMESTROL AND COSMETIC PRODUCT CONTAINING SAME

This application is a 371 of PCT/KR01/01059 filed Jun. 21, 2001.

TECHNICAL FIELD

The present invention relates to 3,9-diferulylcoumestrol and a skin cosmetic product containing the same, more particularly to a novel skin cosmetic product capable of improving anti-aging, whitening and hair-seedling effect and remedying skin disorder from a cosmetic point of view.

BACKGROUND ART

Skin aging means a condition that wrinkles or droops are formed with age. The latest study about skin aging is largely divided into two ways; a histological approach studying for example the mechanism of matrix formation or destruction of connective tissue such as skin collagen and a immunological approach studying for example the relation between oxidizing stress and aging.

At first, the cause of skin wrinkle and droop in a histological viewpoint, is degeneration of collagenous fiber or ellastin fiber[M. Oshima et al., Matrix, 13, 187(1993); S. Harumiya et al., J. Biocham., 120, 745(1996)]. Further, the lowered supporting force of hypodermic tissue and muscle tissue increases wrinkle. In particular, collagen, which is the original material or collageneous fiber and ellastin, is synthesized in fibroblast and forms collagenous fiber and ellastin.

Cell membrane of fibroblast has signal receptor glycoprotein capable of specifically recognizing nutrition passage and extracellular materials. The receptor is connected to ion transport passage and if the exterior materials approaches the receptor of the fibroblast cell membrane, the signal is transported into the cell, finally to the inside of the nucleus. It is ordered to synthesize collagenous protein and more proteins than ordinary state are synthesized and released out of the nucleus. The protein grows by passing through the various organs of the cell and released from the cell. The released protein becomes a base of collagenous fiber or ellastin among cells and then elastic skin with a strong supporting power. [A. Hayasho et al., Fragnance J., 2, 32(1992)]. However, collagen biosysthesis in corium sharply decreases with age and various stress such as ultraviolet rays or environment pollution, resulting in forming wrinkle.[M.Oshima et al., Matrix, 13, 187(1993)].

In immunological viewpoint, oxidative stress in or out of human body destroys cells and biological connective tissue, which increases the number of wrinkles and makes them deeper. Furthermore, as the bio-synthetic ability of the biological anti-oxidant materials becomes lowered with age, the activation of oxidizing materials such as active oxygen which is introduced out of the body or metabolically inevitably generated cannot be prevented, resulting in accelerating wrinkle formation.[L. H. Kligman et al., J. Invest. Dermatol. 93, 210 (1989); H. Tanaka et al., Arch. Dermatol. Res., 285, 352(1993); M. D. Carbonare et al., J. Photochem. Photobiol. B. Biol., 14, 105(1992); T. Okada et al., Fragnance J., 11,23 (1993)]. Therefore, to prevent oxidization of body including skin, artificial intake or application of anti-oxidant agent is essential.

There are a number of materials with anti-oxidant function in nature. The principle of anti-oxidant function could be explained in the following way. Lipids forming cell membranes are easily attacked by peroxides or other active oxygen species generated from environmental factor such as ultraviolet rays or pollution or internal factor such mental stress. They are changed into peroxide lipid and forms radical polymer, resulting in destruction of cell membrane [T. Shibamoto et al., American Chem Soc 154(1994)]. The destruction of cell membrane protecting intracellular materials causes cell necrosis and skin aging. Anti-oxidant materials is oxidized instead before the cell membrane lipid is oxidized, and prevent lipids from being oxidized. So far, anti-oxidant materials used in cosmetics are various plant extract such as tocopherol and ascorbic aid. However, there is a problem that they are very unstable or do not show enough effect.

In present, for the most part of the functional materials applied to anti-aging cosmetics, the anti-aging effect have been discussed only in the basis of in vitro test results and clinic test results, instead of proving histological improvement, because of technical limitation. That is, the anti-aging materials being developed as cosmetics these days are focused only to the in vitro immunological effect. Therefore, it is not believed that such materials bring a substantial anti-wrinkle effect.

Under the above circumstance, the inventors invented 3,9-diferurylcoumestrol synthesized from ferulic acid and coumestrol with superior anti-oxidant force, which can solve chemical unstability or lack of effect and has histological and immunological effect for restraining aging and wrinkle formation.

DISCLOSURE OF INVENTION

It is not easy to develop materials with a substantial anti-aging function. As described above, the sources and products marketed as an anti-aging concept were concentrated on anti-aging effect, but could not obtain desired effects in practice.

The anti-oxidant effect can protect against the attack of internally generated or externally introduced active oxygen species to some extent However, such function has not guaranteed the substantial anti-aging effect in a histological standpoint, such as visible elimination of wrinkles. Therefore, it has been required to develop materials or products which have immunological anti-aging function by anti-oxidant function and further can accelerate skin collagen generation, so that skin recovering and skin elasticity and wrinkle improvement performance are all excellent The inventors tried to develop material which can intensifies immunological function as a basic direction for anti-aging and histologically improve skin wrinkles. Considering the above, we came to synthesize a new concept of anti-aging material from ferulic acid known as its excellent anti-oxidant ability and coumestrol known as its excellent effect for accelerating collagen synthesis, as precursors.

Ferulic acid exists in asafetida, pine resin, leaf of rice plant, and is known as its antibiotic and anti-cancer ability and mild anti-oxidant property.[M. G. Smart et al., Aust J. Plant Physical. 6, 485(1979)]. Further, it is known as having a thrombus coagulation preventing function and used as an antiseptic of food.[T. Tsukiya et al., Jpn. Lolai 7518621 (1975), C. A.83, 7602v(1975)]. Ferulic acid was extracted from a plant resin and named by H. Hiasiwetz and his colleagues of Australia in 1866 [H. Hiasiwetz et al., Ann. 138, 61(1866)].

The active oxygen species derived from oxygen molecule are essentially generated in the metabolism and their concentration should be maintained in the human body. Too low concentration has a bad effect on the metabolism and too high concentration causes peroxidization of bio-molecules such as cell lipid membranes of the organs[A. M. Kligman et al., J. Am. Acad. Dermatol., 15,836(1986); E. J. Van Scott et al., Cutis., 43, 222(1989)].

Ferulic acid has an mild oxidizing force over various active oxygen species derived from oxygen molecule and an strong oxidizing force over oxidative transitional metals such as Iron ion or Copper ion.[M. G. Smart et al., Aust J. Plant Physiol. 6, 485(1979)]. It is further reported that the Ferulic acid is used for preventing auto-oxidization of natural oil such as linseed oil. Ferulic acid has been proved that it is an active material as an ant-oxidant material in the filed of cosmetic, medicine and food.

However, Ferulic acid has only simple anti-oxidant function and is mainly used as an additive for preventing oxidization of effective components of products by transitional metal or other introduced active oxygen species[T. Tsukiya et al., Jpn. Kokai 751862191975], C. A. 83, 7602v (1975)].

Coumestrol is generally found in leguminous plants and has mild anti-oxidant effect and is known to have anti-inflammation, anti-fungal and anti-virus action [Darbarwar, M., et al., J. Sci. Ind. Res., 35, 297(1982); Jeffrey, B. H. et al., Phytochemical Dictionary, Taylor & Francis, London, pp 418(1933)].

Although its accurate mechanism is not revealed, it is known to accelerate production of connective tissue such as collagen in skin and internal organs and believed to have an anti-aging or anti-wrinkle effect [Bickoff, E. M., et al., J. Anim. Sci., 19,4(1960)]. However, the amount of coumestrol contained in a black soybean is extremely small and thus simple extract method does not lead to desired effect Therefore, the objective of the invention is to develop a new material with substantial anti-aging effect and skin-elasticity improving effect together with whitening effect in cosmetics by producing coumestrol in a mass-synthetic way and connecting it with a material with an excellent anti-oxidant effect such as ferulic acid.

Although about three synthetic method of coumestrol has been known. It is not generalized to synthesize coumestrol. The inventors used one of the three methods [E. M. Bickoff, et al., J. Am. Chem. Soc., 80, 4381(1958)]. The used method is total synthesis consisting of total 7 stages. The present invention produces a material having strong anti-oxidant effect together with anti-aging and whitening effect of skin by accelerating the regeneration of skin connective tissue.

Figure 1:
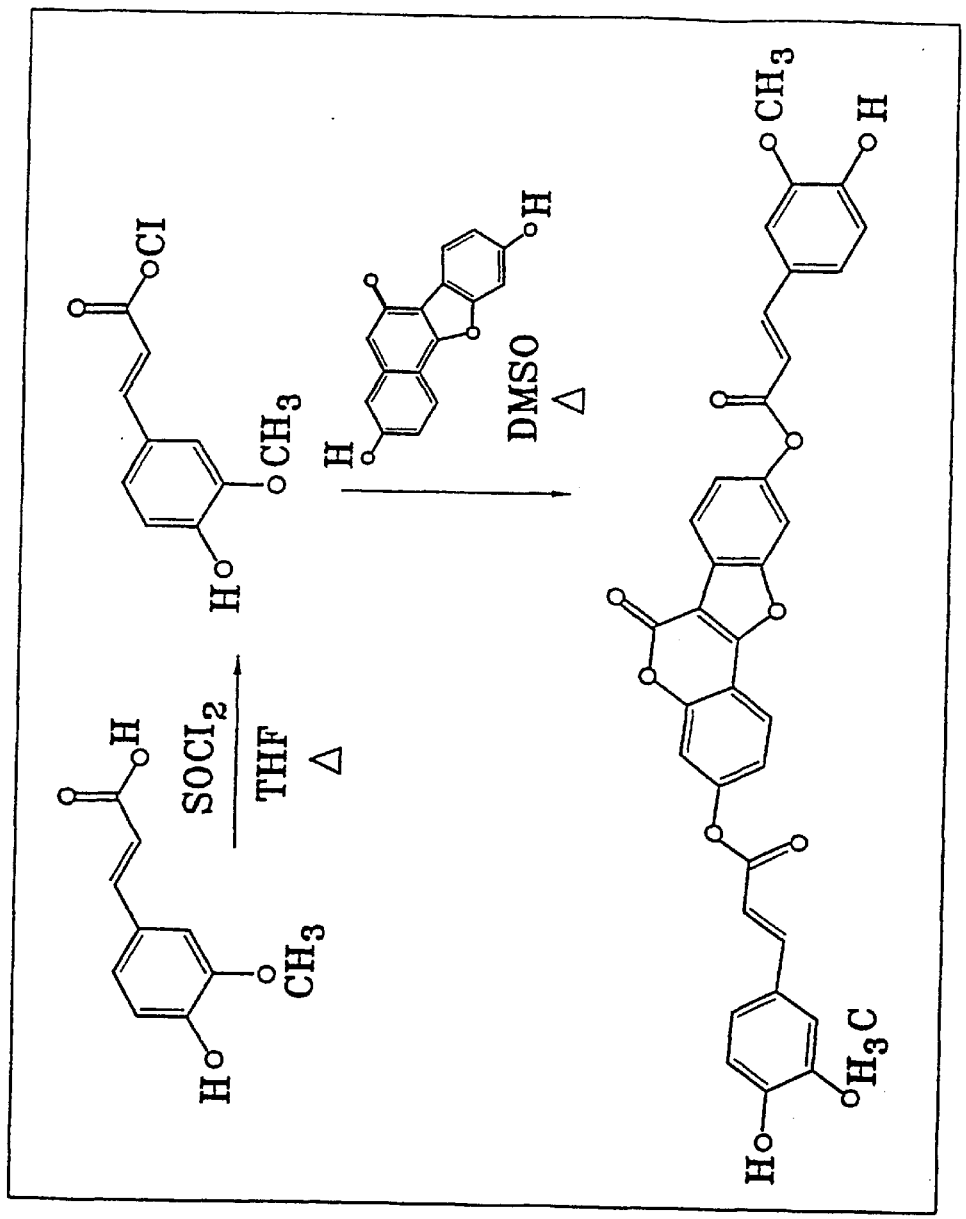
FIG. 1 shows the synthetic method and chemical structure of 3,9-diferulylcoumestrol according to the present invention.

DISCLOSURE OF INVENTION (1) Synthesis of Coumestrol

To investigate the physical and chemical properties of the synthesized materials, melting point was measured using Mel-Temp II(laboratory devices, USA) without correction. For investigating the structure of the synthesized intermediate material and final compound, 1H-NMR spectrum were obtained using Hitachi CW-60 MHz and Varian FT-500 MHz 1H-NMR spectroscope, 13C-NMR spectrum were obtained using Varian FT-500 MHz 13C-NMR spectroscope, IR spectrum were obtained using Jasco FT-IR-5300 spectroscope and UV-VIS spectrum were obtained using Carry UV-VIS spectroscope. Chemical shift was indicated as δ-unit from TMS(tetramethylsilane) as internal standard material, and the data was recorded as "chemical shift(integral strength, multiplicity, coupling constant".

As the $1^{st}$ step for synthesis of coumestrol, 2,4dimethoxybenzaldehyde 50 g, rhodanin 40 g and sodium acetate150 g were dissolved in acetic acid 200 ml and then heated about 130° C. for synthesizing 2,4-eimethoxybenzal-rhodanin. The product is almost insoluble and rapidly became solid in flask. After cooling it, 200 ml of distilled water was added to extract sodium acetate and acetic acid. Then, as the solid product was filtered and washed by excess distilled water until the smell of acetic acid is almost removed. The remained impurities were extracted and removed by about 250 ml of hot ethanol until fine needle yellow products were obtained.

As the $2^{nd}$ step for synthesis of 2,4-dimethoxyphenylthiopyruvic acid, 20 g of 2,4-dimetoxythenzal-rhodanin obtained from the $1^{st}$ step, was floated to the mixture of 80 ml of 15% sodium hydroxide aqueous solution and 20 ml of 14% sodium sulfate, followed by stirring them and heating at 100° C. (about 10 min) in N2 atmosphere until the solid dissolved completely. The mixture was cooled in ice bath and set to pH 2–4 to obtain a precipitate. The precipitate was filtered being washed by distilled water and extracted by 200 ml of ethyl acetate. After removal of the water layer, ethyl acetate was completely concentrated to obtain dark orange needle crystal.

As the $3^{rd}$ step for synthesis of 2,4-dimethoxyphenylpyruvate oxime, sodium methoxylate 18.79 g was dissolved in anhydrous methanol, added by hydroxylaminhydrochloride concentrated aqueous solution and stirred for 5 min to obtain hydroxylamine. After filtering hydroxyl amine solution, 2,4-dimethoxyphenylthiopyruvic acid 24 g was added and refluxed and heated until the sulfide hydrogen was not discharged any more(about 1 hr).

The reacted mixture was cooled and methanol was removed under reduced pressure. Then a very small amount of impurities was extracted by excess 5% sodium hydroxide, and precipitated and filtered. After extracting and removing impurities by adding 200 ml of ethyl acetate in the aqueous solution, its pH was set to 2.0 by 35% HCl aqueous solution to extract the solid product The extracted solid was extracted by 200 ml of ethyl acetate to remove the remained water and the ethyl acetate was again vacuumed concentrated and removed. Finally, it was vacuumed to obtain fine needle crystals As the $4^{th}$ step for synthesis of 2,4-dimethyphenylacetonitrile, the dried oxime 10 g together with anhydrous acetate 6 ml were heated to 100° C. in water bath. They reacted very severely for 2–3 minutes. After they were severely stirred after being added by about 50 ml of distilled water, they were in oil state and then changed into solid immediately. They were washed by thin NaHCO3 aqueous solution and re-distillated by 2-propanol to obtain ivory thick needle crystal.

As the $5^{th}$ step for synthesis of α-(2,4-dimethoxyphenyl)-2,4-dihydroxylacetophenon, 2,4-dimethoxyphenylacetonitrile 4.4 g and resorcinol 8 g were dissolved in 50 ml of anhydrous ether and saturated with HCl gas for about 2 hours, then maintained at 0° C. for 5 days. Ketimin salt precipitated in ether solvent was filtered and introduced in distilled water, then heated until transparent board-shaped precipitates are formed at 100° C. The precipitates were filtered and vacuum dried in desiccator filled with blue silica.

As the 6$^{th}$ step for synthesis of 3(2,4-dimethoxyphenyl)-4,7-dihydroxycoumarin, α-(2,4-dimethoxyphenyl)2,4-dihydroxyacetophenon 6.69 g and methylchloroformate 4.1 ml were refluxed and heated in 150 ml of anhydrous acetone for 4 hours. The reactive mixture were cooled and thinned by 300 ml of distilled water, and acidified by 35% HCl. The produced precipitate was filtered, acetone was remove by vacuum-evaporating the remained liquid and the remained precipitate in the remained liquid was filtered. The precipitate was dissolved in 100 ml of methanol, a small amount of alizarin yellow was added and 20% potassium hydroxide in methanol was added until the indicator became dark yellow, while heating it N2 atmosphere, followed by further being heated for 10 minutes.

The reacted mixture was cooled, and added by 200 ml of distilled water and then acidified by 35% HCl to obtain precipitate. The precipitate was recrystallized to obtain white powder. As a final step for synthesis of coumestrol, coumarin 1.00 g obtained in the 6$^{th}$ step and anilinehydrochloride 2 g were heated at 210–220° C. for 4 hours in N$_2$ atmosphere. The cooled reactant mixture was washed by distilled water for removing aniline hydrochloride and dark-pink impurities were removed by a small amount of ethyl acetate and acetone.

After being purified to some extent, it was dissolved in a mixture of acetone and methanol and heated with 150 mg of active carbon for 10 minutes. The active carbon was filtered by celite filled filter, and it was vacuum concentrated until about 200 ml of solvent remained. The remained solvent was stayed at normal temperature and the obtained precipitate was filtered. The filtered coumestrol was completely dried in vacuum dessicator. To confirm the materials obtained in the respective step and their purities, their melting points and various spectrum data were analyzed and compared to the references.

As for 2,4-dimethoxybenza-rhodanin synthesized in the 1$^{st}$ step, m.p. was 270–273° C. (275° C. in reference) and yield was 90%.

As for 2,4-dimethoxyphenylthiopyruvic acid synthesized in the 2$^{nd}$ step, yield was 86% and m.p. was 166–168° C.(168–170° C. in reference).

As for 2,4-dimethoxyphenylpiruvate oxime synthesized in the 3$^{rd}$ step, yield was 91% and m.p. was 149° C.(149 in reference). In FT-IR spectrum, peak was found at 3232, 3077, 2961, 1697, 1616, 1588, 1509, 1467, 1422 and 1210 cm$^{-1}$. In 1H-NMR(DMSO-d$_6$, 60 MHz), peaks were checked at 6.89(1H.m), 6.50(2H.m), 3.80(3Hs), 3.75(3H.s) and 3.70(2H,s) ppm.

As for 2,4-dimethoxyphenylacetonitrile synthesized in the 4$^{th}$ step, yield was almost quantitative, Rf was 0.70 (hexane:ethylacetate=1:1) and m.p. was 76° C. (76° C. in reference). FT-IR(IBr) spectrum peak was found at 2952, 2848, 2244, 1620, 1509, 1413, 1267, 1217, 1044 cm$^{-1}$ and 1H-NMR(CDCl$_3$, 60 Mhz) peak was found at 7.24(1H,d, 9.6 Hz), 6.50(2H,m), 3.85(3H,s), 3.81(3H, s), 3.60(2H.s) ppm.

As for α-(2,4-dimethoxyphenyl)-2,4-dihydroxyacetophenon synthesized in the 5$^{th}$ step, yield was 35% and Rf was 0.36(hexane:ethylacetate=1:1) and m.p. was 155° C. (156° C. in reference). FT-IR(KBr) spectrum peak was found at 3261, 3006, 2951, 1634, 1507, 1235, 1154, 1134 cm$^{-1}$ and 1H-NMR(CDCl$_3$, 60 Mhz) peak was found at 7.78(1H,m), 7.03(1H,m), 6.4(4H,m), 4.10(2H,s), 3.75(6H.d) ppm.

As for 3-(2,4-dimethoxyphenyl)4,7-dihydroxycoumarin synthesized in the 6$^{th}$ step, yield was 87% and Rf was 0.30(hexane:ethylacetate=1:1) and m.p. was 260–263° C. (263–264° C. in reference). FT-IR(KBr) spectrum peak was found at 3343, 3121, 2968, 2941, 2851, 1689, 1622, 1514, 1277 cm$^{-1}$ and 1H-NMR(DMSO-d$_6$, 60 Mhz) peak was found at 7.78(1H,m), 7.15(4H,m), 7.70(4H,m), 3.82(3H,s), 3.75(3H.s) ppm.

As for coumestrol synthesized in the final step, yield was 70% and Rf was 0.54(hexane:ethylacetate=1;1) and m.p. was 382–383° C. (385° C. in reference). FT-IR(KBr) spectrum peak was found at 3377, 1705, 1631, 1499, 1264, 1092, 1014 cm$^{-1}$ and 1 H-NMR(DMSO-d$_6$, 500 Mhz) peak was found at 7.80(1H, d,8.42 Hz), 7.66(1H, d, 8.42 Hz), 7.15 (1H, d, 2.20 Hz), 6.91(3H,m) ppm.

13C-NMR(DMSO-d$_6$, 100 MHz) spectrum peak was found at 165.23, 163.45, 162.75, 161.57, 159.90, 158.60, 126.64, 124.57, 118.55, 117.82, 117.74, 108.10, 107.05, 105.99, 102.66 ppm, which shows that the synthesis was well performed.

The 5$^{th}$ step yield was low, which was also found in reference. Therefore, the reaction time was doubled and the reaction temperature was raised, which was not effective. It is believed that the reaction is parallel to the kinetic side and does not proceed well. Generally, total yield was about 15%.

BEST MODE FOR CARRYING OUT THE INVENTION

Embodiment 1

Ferulic Ester Derivative, Synthesis of 3,9-diferulylcoumestrol

In order to obtain a new synthetic material, 3,9-diferulylcoumestrol through esterfication of ferulic acid and coumestrol, ferulic acid was purchased from Sigma and coumestrol was synthesized in the above-described method.

As a method for conform the physical property of the synthesized materials, m.p. was determined using Mel-Temp II(laboratory devices, USA), without correction. The structures of the synthesized materials were confirmed using Bruker FT-300 MHz 1H-NMR spectrometer, Bruker FT-75 MHz 13C-NMR spectrometer, Jasco FT-IR 5300 spectrometer and UV-VIS spectrometer. Chemical shift was indicated by δ-unit from an internal standard material TMS (tetramethylsilane) and the data was recorded as "chemical shift(integration intensity, multiplicity, coupling constant (Hz)".

The synthetic method will be explained in detail. A condenser connected with gas absorbing tube was attached to 100 ml 2 branched round flask and ferulic acid 152 mg and THF 5 ml were added and the ferulic acid was completely dissolved. Then, it was added by thionylchloride 110 mg and heated and stirred in water bath. A small amount of the sample was collected at 30 minute intervals and heated with methanol for 1 minute. Then, TLC test for checking the existence of the unreacted materials was carried out to determine the end point of the reaction(about 1 hour). After the reaction ended, THF was vacuum-dried and coumestrol 100 mg and DMSO 15 ml were added and completely dissolved. While heating and stirring it, TLC test was carried out at 1-hour intervals to check the reaction. After the reaction ended, the reactant cooled at room temperature was added by 5% sodium bicarbonate aqueous solution 20 ml and stirred for 10 minute. Then, it was filtered to remove insoluble solids. The filtered liquid was added by 5% hydrochloride to set pH value to 6–7 and the final product was extracted. The extracted product was filtered and washed by distilled water several times to remove acid and base, then vacuum-dried in a dessicator filled with silica gel for 1 day to obtain brown compound(FIG. 1).

The melting point was above 400° C. FT-IR(KBr) spectrum peak was found at 3423, 2943, 1728, 1633, 1597, 1508, 1417, 1499, 1257, 1118, 1030 $cm^1$ and 1H-NMR(DMSO-$d_6$, 300 Mhz) peak was found at 7.91(1H,d), 7.86(1H, d), 7.77(1H,m), 7.72–7.68(2H,m), 7.58–7.44(3H,m), 7.29–7.27 (4H,m), 7.02–6.97(2H,m), 6.84–6.64(2H,m), 3.87(3H,s), 3.85(3H,s) ppm.

13C-NMR(DMSO-$d_6$, 100 MHz) spectrum peak was found at 165.20, 163.38, 162.55, 161.02, 159.10, 158.24, 156.24, 152.20, 150.82, 149.80, 148.48, 146.19, 145.27, 134.06, 129.47, 127.21, 126.71, 125.80, 125.55, 124.60, 122.58, 118.01, 117.66, 117.58, 115.99, 115.56, 114.16, 111.12, 110.45, 107.84, 107.38, 106.12, 102.56, 100.94, 98.45, 56.20, 55.98 ppm. These date shows that a compound with a high purity was synthesized.

Embodiment 2

Measuring of Whitening and Anti-oxidant Activity of Ferulic Ester Derivatives

The synthesized 3,9-diferulylcoumestrol was dissolved to 1,3-butylenglycol so as to produce 0.1%(wt/wt) solution. And whitening activity and anti-oxidant activity were measured by determining tyrosinase inhibition effect and using NBT method. 0.1% vitamin C, 0.1% vitamin E, kojic acid and albutin were used as sample.

For measuring whitening effect of the present invention, 100 ml of 0.2 mg/ml l-tyrosine solution and 5 ml of 680 units/ml tyrosinase solution(3,400 units/mg was diluted 5 times). A solution for blank test was tyrosine 1 ml+phosphoric acid buffer 1 ml+distilled water 1 ml. The procedure of the test is as follows.

TABLE 1

| Used material | Control | Blank test | Test |
| --- | --- | --- | --- |
| Tyrosine(0.2 mg/ml) | 1 ml | 1 ml | 1 ml |
| Buffer(0.1 M, pH 6.86) | 1.9 ml | 1.1 ml | 1 ml |
| Sample | | 0.9 ml | 0.9 ml |
| Tyrosinase(680 units/ml) | 0.1 ml | | 0.1 ml |

1) A,B and C are mixed and maintained at 37° C. for 30 min.
2) D is added and maintained for just 30 min.
3) After 10 min±10 sec, they are took out and the reaction ends in a refrigerating condition by ice.
4) when comparing the absorbance the comparative samples, the absorbencies of comparative group are tested and then those of blank test group are test(at 475 mm).

Tyrosinase activity inhibition effect(%) us calculated in the following way and the result is shown as Table 2.

Tyrosinase activity inhibition effect (%): [1−(E−B/C)]×100

(B: blank test group, C: control group, E: test group)

In the result, the tyrosinase inhibition effect of 3,9-diferuliccoumestrol was greater than that of vitamin C or albutin, though it was smaller than that of kojic acid. The result shows that 3,9-diferuliccoumestrol can be used as whitening material.

TABLE 2

| Sample | Tyrosinase inhibition effect (%) |
| --- | --- |
| 3,9-diferuliccoumestrol | 76 |
| Ascorbic acid | 30 |
| Kojic acid | 91 |
| Albutin | 40 |

To determine anti-oxidant effect, activated oxygen produced from xanthine and xanthine oxidase were measured using NBT method and activated oxygen removal effect of the tested materials was determined. Activated oxygen was produced by xanthine and xanthine oxidase. The activated oxygen was determined by measuring the blue color produced from the reaction of the activated oxygen and Nitroblue tetrasolium (NBT) at 560 nm of wavelength.

The following samples were used.

1) 0.05M(50 mM) $Na_2CO_3$ buffer(MW=105.99): a solution in which 5.25 g(50 mM) of $Na_2CO_3$(Wako Pure Chemical Ind.,Ltd) dissolved in purified water and 50 mM $NaHCO_3$(MW=84.01) were mixed and set to pH 10.2.
2) 3 mM xanthine solution: xanthine(Nakarai chemical MW=152.11) 45.6 mg was dissolved and set to be 10 ml.
3) 3 mM EDTA solution: sodium ethylendiamintetraacetate (Tojin chemical, mw=60.1) was dissolved and set to be 3 mM.
4) 0.15% BSA solution: BSA(Fraction V, powder, Sigma) 15 mg was dissolved and set to be 10 ml.
5) 0.75 mM NBT solution: nitrobluetetrasolium (MW=817.65, Tokyo chemical) 61.32 mg was dissolved to distilled water and set to be 100 ml.
6) Xanthines oxidase solution: xanthine oxidase (Boehringer) was diluted about 100 times so that its blank test absorbance within the range of 0.2–0.23. In other word, the purified water was diluted so that the absorbance change be A560=0.3/20 min.
7) 6 mM $CuCl_2$ solution: $CuCl_2$—$2H_2O$(MW=134.45) 102.29 mg was dissolved to distilled water and set to be 100 ml.

The following measuring method was used.
1. 0.05M Na2CO3—2.4 ml
2. 3 mM Xanthine solution—0.1 ml
3. 3 mM EDTA solution—0.1 ml
4. BSA solution—0.1 ml
5. 0.72 Mm NBT solution—0.1 ml
6. Xanthine oxidase solution 0.1 ml
7. 6 mM CuCl2 solution—0.1 ml
   (1) 1,2,3,4 and 5 are introduced into vial bottle and 0.1 ml of sample solution is added, which are maintained at 5° C. for 10 min.
   (2) It is added by 6 and stirred immediately, followed by 20 min of culture at 25° C.
   (3) After 7 is added, the reaction is stopped. Then, absorbance (St) at 560 nm is measured.
   (4) Blank test is carried out in the same way except distilled water is used instead of sample solution and absorbance (Bt) is measured.
   (5) Blank test for sample is carried out in the same way except distilled water is used instead of 6 and absorbance (Bo) is measured.

The effect is calculated in the following way. The result is shown in Table 3.

Suppression ratio (%)=[1−(St−So)/(Bt−Bo)×100

St: absorbance of sample solution at 560 nm after enzyme reaction

Bt: absorbance of blank test solution at 560 nm without enzyme reaction

So: absorbance of sample solution at 560 nm before reaction without enzyme addition Bo: absorbance of blank test solution at 560 nm before reaction without enzyme addition The result shows that its anti-oxidant force is similar to tocopherol which known as anti-oxidant agent. However, the anti-oxidant force of Vitamin C could not be measured because its anti-oxidant force is so strong that it reacts with the other regent used for measuring the effect.

TABLE 3

| Anti-oxidant activity of 3,9-diferulylcoumestrol | |
|---|---|
| Sample | Anti-oxidant effect (%) |
| 3,9-diferulylcoumestrol | 42 |
| Tocopherol | 43 |
| Vitamin C | Unable to measure |
| Coumestrol | 28 |

EXAMPLE 3

Cell Toxicity and Activity of 3,9-diferulylcoumestrol

Test cells of human-derived fibroblast(ATCC, Hs68) were cultivated in DMEM medium added by 10% FBS at 37° C. in the condition of 5%CO2, 100% humidity. $1 \times 10^5$ cells/ml of cells were seeded in 96 plate and incubated at 37° C. for 24 hr. Samples sterilized by 0.2 m filter were added according to the fixed concentration and further incubated at 37° C. for 24 hr. Then, MTT regent was added and incubated at 37° C. for 4 hr, then the culture solution was removed. After, 1N NaOH isopropane solution was added and stirred for 20 min, the absorbance at 565 nm was measured. Then, the cell apoptosis concentration was determined by comparing the untreated cell (survival ratio: 100%).

50 $\mu$ M of 3,9-diferulylcoumestrol in 1,3-butylenglycol was diluted gradually to find the concentration which does not show cell apoptosis. As a result, cell apoptosis did not show in the range to 78 $\mu$ M (0.0048%). Cell activity at $LD_{50}$ was 20%, which was satisfactory level.

TABLE 4

| | | Coumestrol | Evaluation |
|---|---|---|---|
| $LD_{50}$ | % concentration | 0.0048% | Safe |
| | mole concentration(mM) | 78 $\mu$M | |
| Cell activity | | 20% | Cell activity is excellent |

EXAMPLE 4

Collagen Formation Effect of 3,9-diferulylcoumestrol(Skin Tissue Test for Collagen Proliferation Promoting Effect)

To confirm the collagen formation effect of the synthesized 3,9-diferulylcoumestrol, 10 female hairless mice of 8week age were prepared. From the 2 mice, skin was taken out and standard dye samples were prepared using the side and middle part of the skin for investigation the collagen proliferation level. The other 8 mice were divided into two for the applied group and the control group.

In the same test condition, the whole body except head and belly of the applied group and the control group and were applied by 3,9-diferulycoumestrol 0.1%(wt/wt) 1,3-BG solution and 1,3-BG solution, for 15 days and 30 days.

Figure 2:
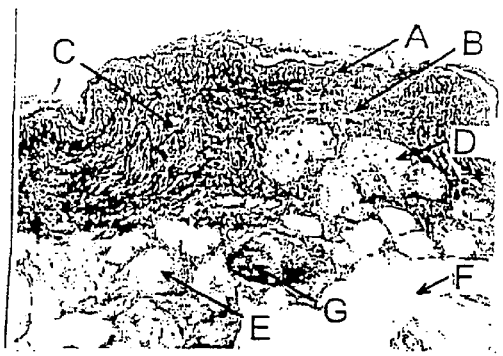
FIG. 2 shows a histological test result about collagen increase in the skin of hairless mice of 1st group in which 3,9-diferulylcoumestrol of the present invention is applied and of control group, respectively.(A: protoplasm, B: collagen(blue), C: nucleus, D: sebaceous glands, E: sweat-gland, F: fat, G: nerve layer).
Figure 2:
Figure 2:
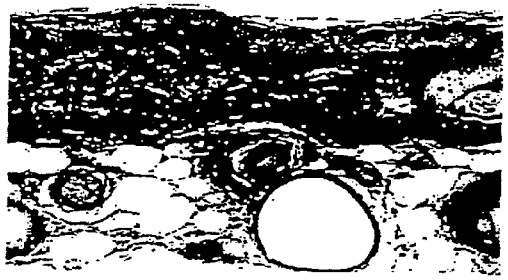
Figure 2:
Figure 2:

From the applied group and the control group respectively, 2 mice were selected and their skins were cut out, then dyed samples were obtained from the side and middle part of the skin. After 30 days, skin dyed samples were obtained in the same way. For each of the obtained 10 dyed skin samples of the control group and the applied group, collagen proliferation promoting effect were compared on the basis of the skin condition of &week age. After 2 weeks, collagen synthesis and proliferation were found in the 3,9-diferulylcoumestrol compared to the initial 8-week age of control group and 1,3-butylenglycol applied control group. In 3,9-diferulylcoumestrol applied group after 30 days, collagen proliferation in corium layer was increased and the tissue density was raised. From the result, it was experimentally confirmed that 3,9diferulylcoumestrol is excellent in collagen synthesis and collagen proliferation promotion(FIG. 2)

EXAMPLES 5, 6 AND 7

In these examples, the cosmetics containing the 3,9-diferulylcoumestrol according the Example 1 were clinically compared. The cosmetic preparation for the clinic test was cream as in Table 4.

First, the B phase on Table 5 was heated and maintained at 70° C. Then, it was added by the A phase for pre-emulsification and then uniformly emulsified by homomixer, followed by slow cooling for preparing creams (Examples 5–7, comparative Example).

The respective creams of Table 5 were applied to the right face of 5 tested female subjects(20–35 years old) 2 times per day for 1 month. After the test were completed, their face color was compared using image analyzer and evaluated under the following standard; the darkest is 5, the middle is 3 and the brightest is 1.

Table 6 compares the face colors of the test subject who used the cream of Example 5 and the test subject who used the cream of Comparative Example.

As shown in Table 6, the face of the subject who used 3,9-diferulylcoumestrol contained cream showed better skin color improvement effect.

TABLE 5

| cream composition | | | | | |
|---|---|---|---|---|---|
| | | Example (wt %) | | | Comparative example |
| Ingredient | | 5 | 6 | 7 | (wt %) |
| A | Stearyl alcohol | 8 | 8 | 8 | 8 |
| | Stearic acid | 2 | 2 | 2 | 2 |
| | Cholesterol stearate | 2 | 2 | 2 | 2 |
| | Squalane | 4 | 4 | 4 | 4 |
| | 2-octyldodecylalcohol | 6 | 6 | 6 | 6 |
| | polyoxyethylene (20 mlol added) alcohol ester | 3 | 3 | 3 | 3 |
| | glycerylmonostearate | 2 | 2 | 2 | 2 |

TABLE 5-continued cream composition

| Ingredient | | Example (wt %) 5 | 6 | 7 | Comparative example (wt %) |
|---|---|---|---|---|---|
| B | 3,9-difeurlylcoumestrol | 10 | 5 | .05 | — |
|  | propyleneglycol | 5 | 5 | 5 | 5 |
|  | purified water | Added to 100 wt % | | | |

TABLE 6

Test result of the cream

| | A | B | C | D | E |
|---|---|---|---|---|---|
| Right face color (Example 5 cream was used) | 2.5 | 2.5 | 3 | 2.5 | 1.5 |
| Left face color (Comparative Example cream was used) | 3 | 3 | 3 | 3 | 2.5 |

The result shows that the present invention has excellent skin improving effect

EXAMPLE 8

95% ethanol 8 g, polypyrrolidone 0.05 g, oleilalcohol 0.1 g, polyoxyethylenemonooleate 0.2 g, perfume 0.2 g, methylparaoxybenzoate 0.1 g, a small quantity of antioxidant and a small quantity of pigment were mixed and dissolved. The mixed solution was added to the 0.05 g of 3,9-diferurylcoumestrol of Example 1 and 5 g of glycerin in 85.33 g of purified water, and stirred to provide cosmetic water with skin improvement effect.

EXAMPLE 9

Cetylalcohol 1.2 g, squalane 10 g, Vaseline 2 g, ethylparaoxybenzoate 0.2 g, glycerinmonoestearate 1 g, polyoxyethylene(20 mol added)mono 1 g and perfume 0.1 g were mixed and heated at 70° C. And 3,9-diferulylcoumestrol 0.5 g of Example 1, diprophyleneglycol 5 g, polyethyleneglycol 1500 2 g, triethanolamine 0.2 g and purified water 76.2 g were dissolved at 75° C. The two solutions were mixed and emulsified, then cooled to provide water/oil solution with skin improvement effect.

EXAMPLE 10

95% ethanol 5 g, polyoxyethylenesorbitanemonooleate 1.2 g, kitullose 0.3 g, hyaluronic acid 0.2 g, vitamin E acetate 0.2 g, glycyrrizinic acid 0.2 g, ethylparaoxybenzoate 0.1 g, 3,9diferurylcoumestrol 1 g of Example 1 and a proper quantity of pigment were mixed to provide a cosmetic solution with skin improvement effect.

3,9-diferurylcoumestrol according to the present invention not only has excellent whitening effect and anti-oxidant effect but also is very safe, and can be applied to various cosmecautical cosmetics.

What is claimed is:

1. A compound comprising 3,9-diferulylcoumestrol.
2. A skin cosmetic composition comprising 3,9-diferulylcoumestrol and the balance being cosmetically acceptable excipients.
3. A cosmetic composition according to claim 2, comprising 0.01–10 wt. % of 3,9-diferulylcoumestrol.
4. A method for restraining wrinkle formation of skin comprising applying to skin an effective amount of a cosmetic composition comprising 3,9-diferulylcoumestrol.

* * * * *